United States Patent [19]

Anderson

[11] Patent Number: 4,686,103

[45] Date of Patent: Aug. 11, 1987

[54] METHOD OF MANAGING CATTLE BREEDING HERDS

[75] Inventor: Lloyd L. Anderson, Ames, Iowa

[73] Assignee: Iowa State University Research Foundation, Inc., Ames, Iowa

[21] Appl. No.: 759,474

[22] Filed: Jul. 25, 1985

[51] Int. Cl.$^4$ .................. A61K 37/24; A61K 31/557; A61K 31/565

[52] U.S. Cl. .......................................... 424/97; 514/2; 514/21; 514/171; 514/573

[58] Field of Search ............... 424/97; 514/2, 21, 171, 514/573

[56] References Cited

PUBLICATIONS

Perezgrovas et al, cited in Chem. Abstracts, vol. 97:1018b, 1982.
Butler et al, cited in Chem. Abstracts, vol. 99:33310y, 1983.
Kostov et al, cited in Chem. Abstracts, vol. 98:119843r, 1982.
Wagner, "Parturition Induction in Cattle", in Current Therapy in Theriogenology, 1980, pp. 236–238.
Perezgrovas and Anderson, Biol. Reprod. (1982), 26:765–776.
Perezgrovas et al., (1982).
Davis et al., J. Anim. Sci., 49:560–566 (1979).
Welch et al., New Zeal. Vet. J., (1979), 25:111.
Diskin, Vet. Record., (1982), 110:268.
Lauderdale, Annal. Biol. Anim. Biophys., (1975), 15:415.
Johnson, Acta. Vet. Scand., (1981), 77:311.
Henricks et al., J. Anim. Sci., (1977) 44:438.
Veznik et al., Am. J. Vet. Res., 40:425 (1979).

*Primary Examiner*—Johnnie R. Brown
*Assistant Examiner*—Jacqueline M. Stone
*Attorney, Agent, or Firm*—Tilton, Fallon, Lungmus & Chestnut

[57] ABSTRACT

Cattle breeding herds are managed for accelerated time-controlled calving, using groups of cows predicted to calve within a period of 10 days, 1000 to 10,000 units of purified porcine relaxin are administered intramuscularly or intracervically. Auxiliary agents may also be administered such as methasone or dexamethasone. Within the selected group, parturition can be limited to time periods as short as 24 to 48 hours. Further, parturition can be accelerated from 2 to 10 days. These benefits are obtained without adverse side effects such as retained placenta or dystocia.

4 Claims, No Drawings

METHOD OF MANAGING CATTLE BREEDING HERDS

FIELD OF INVENTION, BACKGROUND, AND PRIOR ART

The field of this invention is the administration of hormones to pregnant cattle for modification of calving. The method is particularly concerned with the administration of relaxin around the time of parturition.

Parturition can be induced in cattle by treatment with corticoids: dexamethasone, dexamethasone trimethylacetate, flumethasone and betamethasone (Davis et al., *J. Anim. Sci.*, 49:560–566 (1979); Welch et al., *New Zeal. Vet. J.*, (1979), 25:111; Diskin, *Vet. Record.* (1982) 110:268; with prostaglandins (PGF); tham salt of $PGF_{2\alpha}$ or its analogs, cloprostenol and fenprostalene (Lauderdale, *Annal. Biol. Anim. Biophys.* (1975) 15:415; Johnson, *Acta. Vet. Scand.* (1981) 77:311; and with estrogens (Henricks et al., *J. Anim. Sci.*, (1977), 44:438. Corticoids and prostaglandins cause dystocia and retained placenta, and estrogen treatment does not reduce the incidence of retained placenta. Oxytocin injections are successful only in those animals that have had sufficient cervical softening (Veznik et al., *Am. J. Vet. Res.*, 40:425 (1979).

The peptide hormone relaxin is biologically active in female mammals. It has been prepared principally by purification from the ovaries of pregnant sows. See, for example, Sherwood et al, *Arch. Biochem. Biophys.* (1974) 160:185–186. The purified porcine relaxin has been studied and sequenced by Dr. Christian Schwabe and associates: *Science* (1977) 197:914–915; *Biochem. Biophys. Res. Comm.* (1976) 70(2):397–405; and *Biochem. Biophys. Res. Comm.* (1977) (2) 75:503–510.

Relaxin is normally produced in the corpora lutea of mammals during late pregnancy and acts in conjunction with estrogen on the structures of the birth canal. Relaxin acts to promote cervical dilation and widening of the birth canal. Purified porcine relaxin administered to cows a few days before expected parturition does induce cervical dilation as the principal effect. See Perezgrovas and Anderson, *Biol. Reprod.* (1982) 26:765–776. A similar effect is obtained in pregnant sows. See Kertiles and Anderson, *Biol. Reprod.* (1979) 21:57–68. Perezgrovas et al. (1982) found that administration of porcine relaxin (3000 U/mg) four days before expected parturition did not significantly reduce the duration of pregnancy. Some shortening of pregnancy was observed with heifers given relaxin intracervically on three consecutive days. The authors observed, however, that the observed "reduction probably is of little biological significance."

SUMMARY OF INVENTION

This invention is based in part on the discovery that the administration of relaxin to cows toward the end of pregnancy can bring about normal calving within 24 to 48 hours after administration, and that this time-controlled acceleration can be obtained during as early as 5 to 10 days before the normal pregnancy term. These discoveries make it practical to utilize relaxin in the management of cattle breeding herds for group time-controlled calving. Further benefits can be obtained when the administration of relaxin is accompanied by glucocorticoid, such as dexamethasone, or a prostaglandin such as cloprostenol.

The present invention involves a practical hormonal regimen for the induction of parturition in cattle with resulting economic benefits. The improved management of the breeding cattle results in a reduction of calf losses, and an earlier postpartum return to breeding. Further, there is a substantially reduced calving interval in the cow herd because calving dates can be selectively advanced. The combination regimen contrary to previous results with glucocorticoids and/or prostaglandin results in a decrease in the incidence of difficult calving and retained placenta.

DETAILED DESCRIPTION

The term "relaxin" as used herein refers to natural mammalian relaxin or synthetic analogs thereof which have the same biological effects as natural relaxin. The reference standard with respect to source and potency is porcine relaxin but relaxin from other mammalian sources can be used.

For recovery and purification of porcine relaxin, the method of Sherwood et al. may be used. See *Arch. Biochem. Biophys.* (1974) 160:185–196. Schwabe et al. also have described methods for the purification and testing of relaxin. See *Biochem. Biophys. Res. Comm.* (1976) 70:397–405.

One unit of purified relaxin is defined as the amount of WL1000 relaxin standard that produces significant increases over control levels of interpubic ligament formation in estrogen-primed immature Swiss-Webster mice. The accepted potency standard for purified porcine relaxin is defined in (WL1000=relaxin standard from Warner-Lambert Pharmaceutical Company, 1000 Units/mg; NIH460=relaxin standard from National Institutes of Health, 460 Units/mg; highly purified porcine relaxin contains 3000 Units/mg; Steinetz et al., *Endocrinology* (1960) 67:102–115; Fields and Larkin, *J. Endocrinol.* (1980) 87:147–152). For example, purified porcine relaxin may typically have a potency of around 3000 units (U) per milligram (mg).

Cattle breeding herds may comprise either dairy cattle or beef cattle. Artificial insemination (AI) may be employed. For conception, the cows must be in estrus, which is usually a period of from 12 to 18 hours, and occurs once during each cycle of 20 to 21 days. Further, not all cows in estrus become fertilized even though AI is employed. Hormones such as prostaglandins or progesterone analogs can be used to synchronize estrus and thereby permit a larger number of cows in a herd to be inseminated and fertilized at the same time.

By keeping records of artificial insemination, normal pregnancy terms can be predicted with great accuracy, since the above limitations do not affect the length of gestation once conception has occurred. With most common beef and dairy breeds being raised in the United States, the so-called "popular breeds," such as Hereford, Angus, Shorthorn, etc., the gestation periods fall within a narrow range from about 280–284 days. Full term usually occurs at days 282–283.

The method of this invention is not limited to special fertilization procedures, artificial insemination or synchronization of estrus. The method of this invention is generally applicable to the managing of cattle breeding herds including range and field cattle. For beef cattle, breeding herds are commonly maintained on the range. The cows are inseminated by releasing bulls into the herds for periods of several weeks. However, although no records are kept with this natural method of breeding, normal delivery dates (full term dates) can still be estimated with reasonable accuracy.

During the latter months of pregnancy, the pregnant range cows can be segregated from the breeding herds, and grouped according to the expected calving dates. Such grouping can be determined by observation of the cows by experienced cattle managers. One of the advantages of the method of this invention is that exact to-the-day precision is not required. For the purposes of this invention, accuracy within 5 to 10 days of the actual dates of calving can be sufficient to practice the method.

In general, the method of this invention involves breeding a herd of cows to obtain pregnant cows in sufficient numbers to permit selection of one or more calving groups with closely related dates of conception among the cows of each group. The pregnant cows are selected for each group so that the projected full-term gestation periods of the cows within the group are within a time span of about 10 days. Each group may comprise 5 to 100 cows or more. Advantageously, however, groups of about 10 to 40 cows are employed.

Having grouped the pregnant cows, as described, the key steps of this method can then be employed. At a selected time prior to natural parturition of the cows in a group, but not over 10 days before the latest predicted full term day, relaxin is administered to the cows in the group. If the initial group is very large, it can be divided for the relaxin administration, subgroups being formed for the time-controlled accelerated calving. Relaxin is preferably administered at around the same time to each animal, viz. a time period of 1-4 hours. The relaxin may be administered by any biologically effective route. Preferred routes are intramuscular injection and intracervical infusion. Dose level corresponding to 1000 to 10000 Units purified porcine relaxin can be used. Preferably a single dose is given to each animal. In an alternative embodiment of the method, two successive doses can be given at a 24 to 48 hour interval. A similar dose level is used for each administration, such as 1000 to 6000 Units. A preferred dose level is from 2000 to 5000 Units per cow per administration.

It is preferred to administer the relaxin to the cows in the selected group at least two days, and preferably from 5 to 10 days, prior to the earliest predicted full term date of any cow. In addition to advancing the terminations of pregnancy, the delivery of the calves by natural birthing can be obtained in a shortened time span, viz. within 60 hours or less following the administration. In preferred embodiments, the calving is concentrated in a period of 24 to 48 hours after the administration of the relaxin.

In practicing the method of this invention, auxiliary agents can be employed without undesirable side effects. This makes it practical to employ as adjuncts to the relaxin known parturition accelerators, such as glucocorticoids or prostaglandins. For example, the adjunct parturition accelerator may be the corticoid, dexamethasone or the prostaglandin, cloprostenol. Other corticoids which can be employed include dexamethasone, dexamethasone trimethylacetate, flumethasone, and betamethasone. Other prostaglandins include the prostaglandin $F_{2\alpha}$ tham salt ($PGF_{2\alpha}$) or its analogs, such as fenprostalene and cloprostenol. Typical dose levels for intramuscular injection or subcutaneous injection are summarized in the following table.

TABLE A

| Hormone | Effective dosage for induction of parturition |
|---|---|
| Glucocorticoids | |
| Dexamethasone | 20 to 40 milligrams |
| Dexamethasone trimethylacetate | 20 to 30 milligrams |
| Flumethasone | 5 milligrams |
| Betamethasone | 3 milligrams |
| Prostaglandins | |
| Prostaglandin $F_{2\alpha}$ tham salt | 25 to 30 milligrams |
| Cloprostenol | 500 micrograms |
| Fenprostalene | 1 milligram |

Typical dosages of glucocorticoids and prostaglandins for elective induction of parturition in cattle While the auxiliary parturition accelerator can be administered separately, it is convenient to administer it in admixture with relaxin. As indicated, such administration can be by any effective route, such as particularly intramuscular injection or intracervical infusion.

The method of this invention and the results obtained thereby are further illustrated by the following examples.

EXAMPLE I

Materials and Methods

Animals

Forty-seven crossbred beef heifers approaching their first calving were used in this study. All heifers were bred by artificial insemination at estrus (day 0); pregnancy lasts approximately 283 days. Heifers calved at an average age of $25 \pm 1$ months ($\pm$ standard error, SE). Heifers were maintained under pasture conditions during the spring, summer and fall throughout gestation. Mixed silage (6.8 kg/animal/day) supplemented the hay fed during the winter. During the month before calving, corn ($\frac{2}{3}$ kg/animal/day) and mixed silage (9.0 kg/animal/day) were fed in addition to the ad libitum supply of hay.

Experimental groups

Beginning on day 270 of gestation, the animals were assigned randomly to one of three treatment groups; gel vehicle-treated controls, Number (N)=16; single relaxin-treated heifers, N=14; and double relaxin-treated heifers, N=17. A daily blood sample (10 ml) was obtained from a jugular vein via a hypodermic needle (16 gauge, 3.8-cm length). The blood was divided equally into two culture tubes containing 0.1 ml of heparinized saline (10 U/ml), maintained on ice, and centrifuged (2,000 $\times$ g; 4° C.); plasma was decanted into two culture tubes, frozen, and stored at $-20°$ C. for radioimmunoassay of progesterone, estrone ($E_1$), and 17$\beta$-estradiol (17$\beta$-$E_2$). Pelvic and cervical measurements were obtained immediately after the blood collection except on the day of treatment and postcalving, when these measurements were obtained at 12-hour intervals for 60 hours. Relaxin (1 mg, 3,000 U/mg) was infused 4 cm into the cervical os by a sterile insemination pipette on day 278.

Intracervical infusion of relaxin or gel-vehicle

Relaxin was extracted from ovaries of pregnant pigs and purified according to procedures described previously. See Schwabe et al., *Rec. Prog. Horm. Res.* (1978) 34:123. Purified porcine relaxin (3,000 U/mg) was suspended in 1 ml of vehicle prepared by mixing 0.01 molar phosphate buffer saline (M PBS), pH 7.0, and sterile gel (1 ml volume/volume "KY-4", a surgical lubricating jelly, Johnson and Johnson, Inc., New Brunswick, N.J.). Relaxin or gel vehicle was infused by means of a sterile insemination pipette after the cervical probe was withdrawn. A gloved hand was maintained in the reproductive tract of the heifer to guide the pipette through the cervical sphincter. Relaxin or the gel vehicle then was introduced and deposited 4 cm into the cervix.

Cervical dilatation

Dilatation of the cervix was measured intravaginally by using a specially designed stainless-steel probe. The probe consists of 2 12-mm stainless-steel rods anchored to a brass bracked, and the rods are distended by rotating a conical brass swivel. The autoclaved probe was maintained in a glass cylinder with 70% ethanol between measurements of heifers and autoclaved at the end of each series of measurements. Before use, the probe was rinsed with 0.9% NaCl (physiological saline) containing 1,000 U penicillin G/ml. The probe was inserted into the vaginal lumen and guided by a gloved hand into the cervical os to a depth of 3 cm. The tips of the rods were expanded by rotating the conical swivel to a uniform resistance against the cervical wall, then withdrawn, and the separation of the rods was measured.

partum in all (0 of 31) relaxin-treated heifers. In the PBS-gel vehicle-treated heifers, the placenta was retained beyond 24 h in 2 of 16 animals.

Relaxin-induced parturition in beef heifers

Intracervical administration of purified porcine relaxin to primiparous beef heifers during late pregnancy induced marked $P<0.002$) earlier calving than in controls given a PBS-gel vehicle. Relaxin given once (3,000 U) or twice ($2\times3,000$ U, 12 h apart) significantly reduced ($P<0.001$) the interval between treatment and calving as well as increased the percentage of heifers calving within 48 h after treatment. Heifers given relaxin twice calved an average of 3.3 days earlier than PBS-gel vehicle-treated heifers. The duration of gestation was reduced ($P<0.05$) in relaxin-treated heifers as compared with PBS-gel-vehicle controls. Within 24 h after treatment, there were significantly ($P<0.001$) more heifers calving from the relaxin-treated group. The data are presented in Table B.

TABLE B

| | | | | Heifers calving within 48 h after treatment | | Mean interval of days between first treatment |
|---|---|---|---|---|---|---|
| | No. of heifers | Day of Treatment | Day of calving$^a$ | No. | % | and calving |
| Gel-vehicle | 16 | 278.2$^b$ | 283.6 ± 0.9$^c$ | 1$^g$ | 5 | 5.3$^j$ |
| Relaxin-single | 14 | 277.9$^b$ | 280.5 ± 0.8$^{d,e}$ | 6$^h$ | 45 | 2.5$^{k,l}$ |
| Relaxin-double | 17 | 277.4$^b$ | 278.6 ± 1.2$^{d,f}$ | 15$^i$ | 88 | 2.0$^{k,m}$ |

Porcine relaxin, 3,000 U/mg dissolved in a vehicle consisting of 1 ml 0.01 M PBS and sterile gel was administered into the cervical os either once (3,000 U) or twice (2 × 3,000 U, 12 h apart). Controls received 1 ml of gel vehicle intracervically.
$^a$Values are mean ± SE.
$^b$(P > 0.05) = NS.
$^{c,d}$(P < 0.002).
$^{e,f}$(P < 0.05).$\neq^{g,h,i}$(P < 0.001).
$^{j,k}$(P < 0.001).
$^{l,m}$(P < 0.05)

Pelvic area measurements

The area of the pelvic canal was calculated from determination of height and width by using a pelvimeter (Lane Manufacturing, Inc., Denver, Colo.) providing internal landmarks. Pelvic height was determined by measuring the linear distance from the midpoint of the dorsal surface of the symphysis pubis to the ventral surface of the prominent junction of the third and fourth sacral segments. Pelvic widths were determined by measuring the greatest linear distance between depression points in the shaft of the ilia at right angles to the vertical measurements. The pelvimeter was guided by a hand into the rectum to obtain vertical and horizontal measurements. The pelvimeter was cleansed with tap water between successive measurements.

Relaxin effect on pelvic area and cervical dilatation

Pelvic area and cervical dilatation were similar probability, (P>0.05) before relaxin or PBS-gel vehicle treatment. At 12 h after treatment, there were marked increases in pelvic area in all relaxin-treated heifers (P<0.05). These differences in pelvic area between relaxin-treated heifers and PBS-gel vehicle heifers were evident as early as 12 h to 4 days post-treatment. Maximum pelvic opening occurred 12 to 24 h and 24 to 36 h for heifers given relaxin once or twice, respectively. Cervical dilatation increased 11, 526, and 634% within 24 h after the administration of PBS-gel vehicle and relaxin once or twice, respectively (P<0.01). There was no incidence of retained placenta beyond 24 h post- Crossbred beef heifers were bred by artificial insemination and assigned randomly to treatment groups on day 268 of pregnancy. Blood samples were collected daily for radioimmunoassay of relaxin, progesterone, estrone and 17$\beta$-estradiol. Daily measures were obtained of pelvic dimensions and cervical dilation during the prepartum and postpartum periods. On day 272, heifers were given relaxin alone, or in combination with a prostaglandin (e.g., cloprostenol) or a glucocorticoid (e.g., dexamethasone).

Induction of parturition with a glucocorticoid (dexamethasone) and relaxin in cattle: Experimental Plan.

On day 272, 10 days before expected parturition, dexamethasone (20 mg) was administered intramuscularly (im) to 30 first-calf crossbred beef heifers. Relaxin (3,000 Units) was administered either at the same time or 24 h later either im or infused into the cervical os. The relaxin was dissolved in phosphate buffer saline (PBS) for im injection and in PBS plus a sterile gel for infusion in the cervical os. Controls received the dexamethasone im plus either 1 ml PBS im or 1 ml PBS-gel vehicle infused into the cervical os. There were 5 heifers assigned randomly to each treatment group.

Induction of parturition with a prostaglandin (cloprostenol) and relaxin in cattle: Experimental Plan.

On day 272, cloprostenol (500 $\mu$g) was administered im to 30 first-calf crossbred beef heifers. Relaxin (3,000 Units) wad administered either at the same time or 24 h later either im or infused into the cervical os. The relaxin was dissolved in PBS for injection and in PBS plus sterile gel for infusion into the cervical os. Controls received the cloprostenol im plus either 1 ml PBS im or 1 ml PBS-gel vehicle infused into the cervical os. There were 5 heifers assigned randomly to each treatment group.

Induction of parturition with cloprostenol and relaxin in first- and second-calf heifers: Experimental Plan.

The effect of cloprostenol and relaxin or PBS given im on induction or parturition was determined in 16 first-calf and 25 second-calf beef heifers. The 41 heifers were given cloprostenol im plus relaxin or PBS im on day 272 of pregnancy.

Experimental Results

A summary of the experimental results is presented below in Tables C and D. Relaxin administered in combination with dexamethasone induced a highly significant ($P<0.02$) earlier parturition (33 vs 53 h) in first-calf heifers as compared with dexamethasone in combination with PBS. In addition to calving being induced approximately 8 days earlier than the normal duration of gestation, the interval from treatment to parturition was precisely timed in the relaxin-dexamethasone treated heifers as compared with the controls. Calving ease was improved markedly ($P<0.005$) in heifers given relaxin plus dexamethasone (80%) as compared with controls given dexamethasone plus PBS (30%). The incidence of retained placenta was reduced ($P<0.005$) in the heifers given relaxin plus dexamethasone (15%) as compared with the controls (70%). Relaxin treatment decreased the interval to parturition, improved calving ease and reduced the incidence of retained placenta when given either intramuscularly or intracervically at the same time or 24 h after dexamethasone as compared with controls given dexamethasone plus PBS.

Relaxin administered in combination with cloprostenol significantly reduced ($P<0.02$) the interval from treatment to calving (35 vs 54 h) as compared with controls given cloprostenol plus PBS (Table C). Furthermore, the incidence of retained placenta was reduced markedly ($P<0.005$) in heifers given relaxin plus cloprostenol (30%) as compared with the controls (80%).

Overall, relaxin administered either with dexamethasone or cloprostenol significantly reduced the interval from treatment to parturition ($P<0.02$; 34 vs 51 h), improved calving ease ($P<0.05$; 62 vs 35%), and reduced the incidence of retained placenta ($P<0.005$; 23 vs 75%) in first-calf heifers as compared with controls given dexamethasone plus PBS or cloprostenol plus PBS.

The effects of relaxin combined with cloprostenol on the induction of parturition in first- and second-calf heifers are presented in Table D. The interval from treatment to parturition was reduced markedly in first-calf heifers ($P<0.02$) and second-calf heifers ($P<0.01$) given relaxin plus cloprostenol as compared with controls given PBS plus cloprostenol. Calving ease was increased by relaxin ($P<0.05$) in first- and second-calf heifers. The incidence of retained placenta was less ($P<0.05$) in relaxin-treated first-calf heifers; there was no instance ($P<0.001$) of retained placenta in relaxin-treated second-calf heifers. Furthermore, the duration of labor was reduced by relaxin treatment in first-calf heifers ($P<0.05$) and second-calf heifers ($P<0.01$) as compared with controls.

Overall, relaxin combined with cloprostenol effectively reduced the period from treatment to parturition ($P<0.001$), increased calving ease ($P<0.05$), reduced the incidence of retained placenta ($P<0.05$), and decreased the duration of prepartum labor ($P<0.05$) in first- and second-calf heifers as compared with controls given cloprostenol and PBS.

TABLE C

Effect of Relaxin in Combination with Dexamethasone (DEX) of Cloprostenol (CLO) on Induction of Parturition in First Calf Beef Heifers.

| Group | No. of Heifers | Interval between treatment and calving, h$^b$ | Ease of calving, % | Animals with placenta retained ≧24 h, % |
|---|---|---|---|---|
| Relaxin + Dex vs PBS$^a$ + Dex | 30 | 33 ± 2.4 vs 53 ± 2.6$^d$ | 80 vs 30$^e$ | 15 vs 70$^e$ |
| Relaxin + Clo vs PBS & Clo | 30 | 35 ± 3.1 vs 54 ± 3.4$^d$ | 45 vs 40 | 30 vs 80$^e$ |
| Relaxin vs Dex or Clo | 60 | 34 ± 2.8 vs 51 ± 3.0$^d$ | 62 vs 35$^c$ | 23 vs 76$^e$ |

$^a$Phosphate buffer saline.
$^b$Values are mean ± SE.
$^c$P < 0.05
$^d$P < 0.02
$^e$P < 0.005.

TABLE D

Effect of Cloprostenol and Relaxin or Phosphate Buffer Saline (PBS) Administered Intramuscularly on Induction of Parturition in First and Second Calf Beef Heifers

| Group | Treatment | No. of Heifers | Interval between treatment and calving, h$^a$ | Ease of calving, % | Animals with placenta retained ≧24 h, % |
|---|---|---|---|---|---|
| 1st calf heifers | Cloprostenol + Relaxin | 11 | 20 ± 6$^d$ | 82$^b$ | 18$^f$ |
|  | Cloprostenol + PBS | 5 | 46 ± 5$^e$ | 40$^c$ | 80$^g$ |
| 2nd calf heifers | Cloprostenol + Relaxin | 16 | 23 ± 4$^f$ | 100$^b$ | 0$^h$ |
|  | Cloprostenol + PBS | 9 | 44 ± 7$^g$ | 75$^c$ | 100$^i$ |
| 1st & 2nd calf heifers | Cloprostenol + Relaxin | 27 | 27 ± 5$^h$ | 93$^b$ | 8$^f$ |
|  | Cloprostenol + PBS | 14 | 45 ± 6$^i$ | 63$^c$ | 93$^g$ |

$^a$Values are the mean ± SE.
$^{bc}$P < 0.05 within group.
$^{de}$P < 0.02 within group.
$^{fg}$P < 0.01 within group.
$^{hi}$P < 0.001 within group.

I claim:

1. In the management of a cattle breeding herd, the method of accelerating the birth of calves while minimizing the incidence of calving difficulties and retained placenta, consisting essentially of:

(a) prior to parturition of a pregnant cow but not over ten days before the predicted full term date for the cow, administering relaxin to the cow, the relaxin being administered by an effective route at a dose level corresponding to 1,000 to 10,000 units of purified porcine relaxin; and (b) during said time period also administering to said cow a parturition inducing agent selected from the group consisting of glucocorticoids and prostaglandins, said agent being given in an amount effective for accelerating parturition so that parturition occurs for the cow within a period of less than sixty hours.

2. The method of claim 1 in which said relaxin is administered by intracervical infusion, the amount administered corresponding to about 2000 to 5000 units of purified porcine relaxin, and there is also administered concurrently with the relaxin the glucocorticoid dexamethasone in an amount effective for accelerating parturition.

3. The method of claim 1 in which said relaxin is administered by intracervical infusion, the amount administered corresponding to about 2,000 to 5,000 units of purified porcine relaxin, and there is administered concurrently with the relaxin the prostaglandin cloprostenol in an amount effective for accelerating parturition.

4. The method of claims 1, 2, or 3 wherein said parturition inducing agent is given in an amount effective for accelerating parturition so that parturition occurs for the cow within a period of less than forth-eight hours.

* * * * *